United States Patent [19]
Barrett et al.

[11] Patent Number: 6,136,321
[45] Date of Patent: *Oct. 24, 2000

[54] METHOD OF INACTIVATING LIPID-ENVELOPED VIRUSES

[75] Inventors: Noel Barrett, Klosterneuburg/Weidling; Otfried Kistner; Friedrich Dorner, both of Vienna, all of Austria

[73] Assignee: Baxter Aktiengesellschaft, Vienna, Austria

[*] Notice: This patent issued on a continued prosecution application filed under 37 CFR 1.53(d), and is subject to the twenty year patent term provisions of 35 U.S.C. 154(a)(2).

[21] Appl. No.: 09/021,146

[22] Filed: Feb. 10, 1998

[30] Foreign Application Priority Data

Feb. 24, 1997 [AT] Austria ........................................ 299/97

[51] Int. Cl.$^7$ .............................. A61K 39/12; C12N 7/06

[52] U.S. Cl. .................................... 424/208.1; 424/184.1; 435/235.1; 435/236; 435/238; 435/239

[58] Field of Search .............................. 424/184.1, 204.1; 435/235.1, 236, 238, 239

[56] References Cited

FOREIGN PATENT DOCUMENTS

| | | |
|---|---|---|
| 0 037 931 | 10/1981 | European Pat. Off. . |
| 0 564 958 | 10/1993 | European Pat. Off. . |
| 37 04 550 | 8/1988 | Germany . |
| 93/01831 | 2/1993 | WIPO . |

OTHER PUBLICATIONS

Haraud, "Introductory Remarks: Viral Safety Of Biologicals", *Develop. Biol. Standard*, vol. 75:3–7, (1991).

Brown, "Review Of Accidents Caused By Incomplete Inactivation Of Viruses", *Develop. Biol. Standard*, vol. 81:103–107, (1993).

Smith et al., "Laboratory Aspects Of Fourteen Human Cases Following Vaccination And Attempts To Isolate The Virus From The Vaccine", *Am. J. Hyg.*, vol. 63:150–164, (1956).

Mussgay et al., "Preparation Of Inactivated Vaccines Against Alphaviruses Using Semliki Forest Virus—White Mouse As A Model", *Intervirology*, vol. 1:259–268, (1973).

Piet et al., "The Use Of Tri(n–butyl)phosphate Detergent Mixtures To Inactivated Hepatitis Viruses And Human Immunodeficiency Virus In Plasma And Plasma's Subsequent Fractionation", *Transfusion*, vol. 30(7):591–598, (1990).

Danihelkova et al., "Disruption Of Influenza Virus A By Diethylether–tween and Tri–N–Butyl Phosphate–tween Mixtures", *Acta Virol.*, vol. 28:26–32, (1984).

Gross et al., "Comparison Of New Triton X–100–and Tween–Ether–Treated Split–Product Vaccines In Children", *Journal Of Clinical Microbiology*, vol. 14(5):534–538, (1981).

Hennig et al., "Immunization with Tween–Ether–Treated SIV Adsorbed Onto Aluminum Hydroxide Protects Monkeys Against Experimental SIV Infection", *Virology*, vol. 186:588–596, (1992).

Reed et al., "A Simple Method Of Estimating fifty Per Cent Endpoints", *The Journal of Hygiene*, vol. 27(3):493–497, (1938).

Laemmli, "Cleavage Of Structural proteins During The Assembly Of The head of Bacteriophage T4", *Nature*, vol. 277:680–685, (1970).

*Primary Examiner*—Robert D. Budens
*Attorney, Agent, or Firm*—Foley & Lardner

[57] ABSTRACT

The invention relates to a method of inactivating lipid-enveloped viruses by means of a non-ionic detergent, and the preparation of a vaccine containing the inactivated virus. The invention further relates to an inactivated virus which is characterized by its structural integrity, in particular the structural integrity of its enveloping proteins, as well as to the use of the inactivated virus for preparing a vaccine.

16 Claims, 3 Drawing Sheets

METHOD OF INACTIVATING LIPID-ENVELOPED VIRUSES

FIELD OF THE INVENTION

The invention relates to a method of inactivating lipid-enveloped viruses by means of a non-ionic detergent and the preparation of a vaccine containing the inactivated virus. Furthermore, the invention relates to an inactivated virus which is characterized by its structural integrity, in particular by the structural integrity of its enveloping proteins, as well as to the use of the inactivated virus for the preparation of a vaccine.

BRIEF DESCRIPTION OF THE BACKGROUND ART

In the past decades, the development of an efficient vaccine for the prevention of viral infectious diseases has been one of the main objects of medicine. In the preparation of live virus vaccines virus mutants are used which have antigens identical to that of the wild type virus, yet have a reduced pathogenicity or virulence.

To prepare dead vaccines, wild type viruses are inactivated by a physical or chemical treatment, such as with formalin, hydroxylamine, β-propion lactone or UV radiation, the type of inactivation being important, in particular with a view to retaining the immunogenicity of the viral antigens. The technique mostly used for virus inactivation in the preparation of vaccines is the mild treatment of viruses with formalin, which, however, requires a long incubation period of up to 15 days (e.g. in case of HAV) so as to obtain a sufficient reduction of virus activity.

Whole virus vaccines generally stimulate the development of circulating antibodies to the enveloping proteins of the virus. Thus it has repeatedly been pointed out that it must be ensured in this inactivation process that the immunogenicity of the viral proteins is retained. Simultaneously, however, it must be ensured that all the viruses in the preparation are inactivated so as to guarantee safe vaccines.

As a consequence of incidents caused by incompletely inactivated whole virus vaccines or contaminations of the vaccine preparation with cellular components or undesired viral particles, there has been a search for alternative inactivation methods (Horaud, Develop. Biol. Standard. 75 (1991), 3–7; Brown, Develop. Biol. Standard. 81 (1993), 103–107).

Since formalin inactivation is not always complete, and since residual infectious viruses have been found in individual vaccine preparations (Smith et al., Am. J. Hyg. 63 (1956), 150–164), Mussgay et al. (Inter-virology 1 (1973), 259–268) have proposed a two-step inactivation procedure, wherein a formalin inactivation followed upon a treatment with Tween 80/ether, NP 40 or deoxycholate. However, they found that by the additional treatment with the detergent or solvent/detergent, the protectivity of the formalin-inactivated vaccine was negatively affected.

Thus, in recent years, subunit vaccines have increasingly been developed alternatively to vaccines containing inactivated whole viruses. In the preparation of subunit vaccines, the intact virus is solubilized with a strong detergent, the viral proteins are dissolved out of the virus, and selective antigens which are capable of stimulating protective antibodies are isolated and used for vaccine preparation. Simultaneously, non-viral proteins and membrane components of the virus that might have undesired side effects when administering the vaccines are eliminated. The antigens isolated for the subunit vaccines may also be contained in the vaccine in highly purified form and at a high concentration. Yet the immunogenicity may be reduced as compared to a whole virus vaccine, since only individual antigens are available as an immunogen.

To induce a sufficient immune response at vaccination, so-called split vaccines have thus been prepared. There, the virus is completely solubilized with a detergent or with a mixture of a detergent and a solvent, the integrity of the virus is destroyed, and the virus is dissolved into its individual components, such as core proteins, enveloping proteins and membrane components. The thus prepared mixture of viral components is then utilized for vaccination.

Experiments carried out in the course of virus inactivation of human plasma products have shown that a solvent/detergent treatment with TNBP/Tween® 80 is capable of inactivating lipid-enveloped viruses, such as, e.g., HIV, HCV, HBV or Sindbis virus (Piet et al., Transfusion 30 (1990), 591–598).

In the commercial production of influenza virus subunit vaccines, various methods are used for the inactivation with lipid solvents, such as Triton® X-100, cetyltrimethyl-ammonium bromide, TNBP/Tween® 80 or diethyl ether/TweenO 80. Particularly when using diethyl ether in the inactivation step, it has been found that there resulted a marked decrease of the hemagglutinin activity. Danihelkova et al. (Acta virol. 28 (1984), 26–32) found that the hemagglutinin and neuraminidase activities of inactivated influenza virus are retained after a treatment with TNBP/Tween® 80 or diethyl ether/Tween® under certain conditions. They note, however, that removal of the solvent, in particular of diethyl ether, from the preparation poses problems, and therefore an inactivation method using TNBP/Tween® 80 is considered to be preferable.

To avoid the complex removal of the solvent, thus only Triton X-100 was used as non-ionic detergent in the preparation of an influenza split vaccine (Gross et al., J. Clin. Microbiol. 14 (1981), 534–538).

Non-ionic detergents do not have charged groups, the hydrophilic character of these detergents is caused by the hydroxyl group. In contrast to ionic detergents, they solubilize membrane proteins much more mildly. The non-ionic detergent breaks up lipid-lipid and lipid-protein bonds, while protein-protein interactions remain unaffected. By this, the native structure of the proteins is retained. Moreover, the detergent replaces the lipids which normally are connected to the hydrophobic portion of the proteins, whereby a lipid-like environment is created and thus the solubilized proteins are stabilized.

Investigations regarding the protectivity of inactivated SIV vaccines after a treatment with formalin, psoralen, Triton® X-100 or Tween®/ether indicated that formalin and psoralen-inactivated SIV preparations do not protect against an SIV infection and that the Triton® X-100 inactivation yields only partial protection. However, with a Tween® 80/ether inactivated split vaccine of SIV, a protective effect could be shown only at a high antigen dose and in the presence of a potent adjuvant (Stahl-Hennig et al., Virology 186 (1992), 588–596).

Particularly when using infectious human pathogenic viruses for preparing a whole virus vaccine it is necessary to provide an effective and safe method of inactivating the viruses. This particularly holds for such viruses as, e.g., HIV, in which an inactivation with conventional methods has been considered to be insufficient. As mentioned above, in case of SIV, e.g., a formalin inactivation leads to a possible loss of antigenicity.

SUMMARY OF THE INVENTION

Thus, it is the object of the present invention to provide a new method of inactivating viruses which efficiently inactivates lipid-enveloped viruses.

DESCRIPTION OF THE PREFERRED EMBODIMENTS

According to the invention, this object is achieved in that a method of inactivating a virus is provided, wherein a lipid-enveloped intact virus is incubated with a non-ionic detergent from the group of polysorbates for a period of time sufficient to completely inactivate the virus particle, yet without affecting its structural integrity and particularly the biological activity of its surface and enveloping proteins.

Surprisingly it has been found that by treating lipid-enveloped viruses with a non-ionic detergent from the group of polysorbates, the viruses are efficiently inactivated, the structural integrity of the whole virus and in particular of the enveloping proteins as well as their biological activity, such as immunogenicity and antigenicity, at least largely being retained. This was particularly surprising since the use of non-ionic detergents, such as Triton® X-100 has been described in the prior art for the preparation of split vaccines and thus for disintegrating intact virus particles.

Comparative tests carried out within the course of the invention with other non-ionic detergents, such as octyl glucoside, have furthermore shown that this detergent does inactivate all the viruses tested, yet attacks the structural proteins of the virus, in particular the enveloping proteins, and solubilizes them. Since the retention of the biologic activity, in particular the external enveloping proteins, is of decisive importance for the formation of a protective immune response of viral vaccines, the antigenicity and immunogenicity of a vaccine containing a whole virus with solubilized enveloping proteins are impaired as compared to an intact virus.

According to a special aspect of the invention, lipid-enveloped viruses are inactivated when carrying out the method according to the invention. Lipid-enveloped viruses from the group of retroviruses, such as HIV-1 and HIV-2, the flaviviruses, such as TBEV and HCV, the influenza viruses, the herpes viruses, the paramyxo viruses, such as mumps virus and measles virus, or the arena viruses, such as Junin virus and Lassa virus, are particularly preferred.

Furthermore, it has been shown that by the method according to the invention not only the immunogenicity of the antigens and the integrity of the whole virus and of the enveloping proteins are retained, but also that the biological activity of the proteins, such as, e.g., the hemagglutinating activity of influenza virus or TBEV, or the CD4 binding activity of HIV-1, is not affected.

To carry out the method according to the invention, non-ionic detergens from the group of the polysorbates (polyoxyethylene sorbitanes) are utilized. Preferably, polysorbates from the group consisting of Tween® 80, Tween® 60, Tween® 40 and Tween® 20, or combinations thereof, are used. Particularly preferred is the use of Tween® 80 for carrying out the method. In particular, it has been shown that the non-ionic detergents of this group do not attack intact proteins and do not destroy their activity, respectively.

Particularly for a complete inactivation of all the viruses present in a solution it is necessary that an interaction and aggregate formation of the virus particles is avoided, since within an aggregate complex, individual particles may be protected against the action of an inactivating detergent. The present invention thus offers the advantage that the interaction of viruses via a protein-protein-interaction of the surface proteins is reduced and even prevented, and that the individually present virus particles can be directly enveloped and inactivated by the detergent.

To carry out the method according to the invention, a concentration of the polysorbate in a range of between 1% and 25% is used for inactivating the lipid-enveloped viruses. Preferably, the concentration is in a range of between 10% and 20k, or between 10% and 15%, respectively.

Surprisingly it has been found within the scope of the invention that a complete inactivation of the tested viruses had taken place already after a 10 minute incubation with the polysorbate, while a comparable inactivation of, e.g., HIV-1, in a parallel test formulation comprising 0.03 to 0.1% formalin was achieved only after 10 hours.

Thus, according to the invention, the present method for inactivating lipid-enveloped viruses is carried out such that a virus suspension either derived directly from cell culture supernatants or from a purified virus solution, is incubated for at least 10 minutes with the non-ionic detergent from the group of polysorbates. For most of the lipid-enveloped viruses, complete inactivation of the viruses in the solution is achieved already after this period. Yet longer incubation periods of up to 10 hours are possible without any loss of the biological activity and of the structural integrities of the whole virus and of the enveloping proteins.

The period of incubation with the non-ionic detergent which is sufficient to inactivate the virus may be determined by a simple kinetics of the virus inactivation and by determining the virus titer, such as, e.g., described in Example 2 (infra).

Preferably, the method according to the invention is carried out at a temperature of between 20° C. and 40° C. The choice of the optimum temperature range for inactivating viruses with the method of the invention is within the general knowledge of the skilled artisan. Determining an optimum temperature for the method of the invention may thus be effected without any difficulty for the respective combination detergent/virus. Likewise, other parameters, such as the optimum concentration of the non-ionic detergent, the protein concentration and the incubation period, may be determined by any skilled artisan.

In determining the optimum parameters for the method, care must always be taken that the structural integrity and, in particular, the biological activity of the surface and enveloping proteins are not affected. Although an at least 50% retention of the whole viruses originally contained is considered sufficient for this, preferably at least 80%, more preferred at least 90%, in particular 95%, of the virus particles treated according to the invention should retain their structural integrity.

A particular advantage of the method according to the invention thus resides in the rapid and efficient inactivation of the lipid-enveloped viruses, which allows particularly for using the method on a large scale and in the production of inactivated virus vaccines. Since it is known that for the preparation of, e.g., an influenza virus vaccine only a short period is available for virus propagation, inactivation and vaccine preparation, the present invention offers a substantial improvement in the industrial production of a vaccine.

In the production of vaccines, virus inactivation in any event is followed by a sterile filtration so as to remove any possible contaminations, such as cellular components or bacterial impurities, from the solution.

It has been found within the scope of the present invention that sterile filtering of an inactivated virus preparation prepared by the present method is easier, since the glycoproteins of the external virus envelope which normally can bind to the filter membrane have a lower affinity to the filter membrane as a consequence of their binding with the detergent monomers. Thus, the present invention offers the additional advantage that the losses of inactivated virus particles normally occurring during sterile filtration are reduced, and the yield of inactivated viruses for the vaccine preparation is increased.

According to a particular aspect of the present invention, the non-ionic detergent from the group of the polysorbates remains in the virus-containing solution after the inactivation step. Particularly for Tween® 80 it has been known that it is considered to be human compatible and frequently is used in food stuffs and cosmetics. Thus, in a vaccine to be administered to man or animal and comprising a more or less small amount of detergent, no side effects are to be expected. Since according to the present method a concentration of up to 20% of non-ionic detergent can be used for the inactivation of viruses, it is, however, advantageous in some instances to reduce the concentration of detergent in the final product or, optionally, to completely remove it therefrom. This may be effected by known measures, such as, e.g., dialysis or chromatographic procedures. Particularly suitable chromatographic procedures are ion exchange chromatography or gel filtration. However, all the methods described in the prior art for removal of non-ionic detergents from a solution are suitable.

When using viral vaccines that, in particular, are administered orally, there is often the problem that the antigens are destroyed in the stomach by proteolytic degradation and thus lose their effectiveness. As has been known, polysorbates are also considered to be "stabilizing detergents", which allow components present in a solution, in particular proteins, to remain stable in the solution over a longer period of time (WO 93/01831). According to a further aspect of the present invention, the inactivated virus preparation produced according to the invention contains a stabilizing agent. Preferably, the virus preparation contains a polysorbate at a final concentration of at least 0.05%, preferably of from 0.05% to 0.5%, particularly preferred of 0.2%, as the stabilizing agent. It is, however, also possible to remove the detergent used as inactivating agent from the virus preparation and to add any stabilizing agent known from the prior art to the preparation.

A further aspect of the invention relates to a method of preparing an inactivated virus vaccine, wherein inactivated viruses obtained upon inactivation according to the above-described method, optionally after removal of the inactivating detergent, are admixed with a physiologically acceptable carrier and, optionally, with an adjuvant.

Another aspect of the present invention relates to a virus preparation containing an inactivated virus, wherein the virus is characterized by the structural integrity of the whole virus and, in particular, by the integrity of the enveloping proteins. Within the scope of the present invention it has been found that the treatment and inactivation of a lipid-enveloped virus particle with a non-ionic detergent, selected from the group of polysorbates, does not affect the integrity of the whole virus and, in particular, does not influence the biological activity of the enveloping glycoproteins. This was particularly surprising since other non-ionic detergents, such as Triton X-100 or octyl glucosides, inactivate lipid-envloped viruses and thereby destroy the structural integrity of the whole virus.

According to a further embodiment of the invention, the inventive virus preparation optionally contains a stabilizing agent as a further component. According to what has been said above, the stabilizing agent preferably is the non-ionic detergent from the group of polysorbates, in particular Tween® 80, which has been used for inactivation. Any stabilizing agent known from the prior art may, however, be contained.

According to a further aspect, the present invention provides the inventive virus preparation as a medicament, in particular for preparing a stable vaccine for immunizing vertebrates, i.e. a vaccine containing a virus preparation of the above-described type which optionally contains a physiologically acceptable carrier.

According to a further aspect of the invention, the vaccine is comprised of a virus preparation inactivated according to the inventive method, wherein, optionally after the inactivating step, the inactivating non-ionic detergent is removed and a physiologically acceptable carrier is admixed to the inactivated virus solution. According to the present invention, all pharmaceutical formulations known in the prior art are considered as physiologically acceptable carriers. The formulations of the vaccine according to the invention may be effected in a common manner as known per se, e.g. by aid of ionized water, of a phosphate-buffered solution, of salts, and it may optionally contain amino acids or mild, non-ionic detergents, such as Tween® 20 or Tween® 80, for stabilizing purposes.

The inactivated virus may be formulated for use as a vaccine in the most varying manners. The concentration of the inactivated virus in the vaccine generally ranges between $10^6$ and $10^9$ pfu/ml, preferably it lies at $10^7$ pfu/ml. The vaccine according to the invention optionally contains an adjuvant at a desired concentration so as to increase the immune response, e.g. to stimulate the production of neutralizing antibodies. Immunologically acceptable adjuvants thus may be mineral oils, Freund adjuvant, vegetable oils, mineral salts, immunomodulators or immunopotentiators.

The vaccine may be administered in the most varying manners, e.g. subcutaneously, orally, nasally, intramuscularly or intraperitoneally. Generally, the vaccine dose is administered according to known vaccination regimens.

The invention will now be described in more detail by way of the following Examples and the drawing figures, obviously, however, it shall not be restricted to the same.

Example 1 describes the inactivation of lipid-enveloped viruses with non-ionic detergents Tween® 80 and octyl glucoside; Example 2 describes the kinetics of the virus inactivation of HIV-1 and TBEV following treatment with Tween® 80; Example 3 describes the Western blot analysis of inactivated HIV-1 following treatment with 1% octyl glucoside and 15% Tween® 80; Example 4 describes the Western blot analysis of inactivated KP influenza virus following treatment with 1% octyl glucoside and 11% Tween® 80; Example 5 describes the immunization of mice with Tween® 80-inactivated MAIDS complex; Example 6 describes the kinetics of the virus inactivation of HIV-1 with formalin, and Example 7 describes the Western blot analysis of formalin-inactivated HIV-1 after various periods of incubation.

Figure 1:
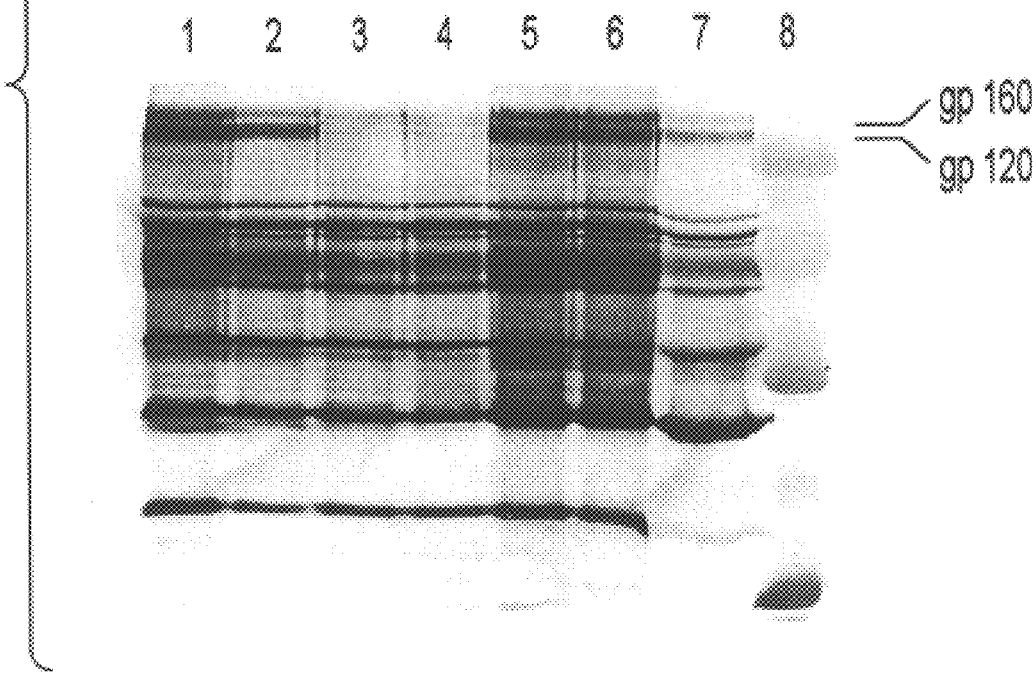
FIG. 1: Western blot analysis of inactivated HIV-1 following treatment with 1k octyl glucoside and 11% Tween® 80.

Table 1: Virus inactivation of lipid-enveloped viruses with non-ionic detergents Tween® 80 and octyl glucoside;

Table 2: Kinetics of the virus inactivation of HIV-1 and TBEV following treatment with Tween® 80;

Table 3: Immune response of mice immunized with Tween® 80-inactivated MAIDS complex after 5 weeks and 12 weeks;

Table 4: Kinetics of virus inactivation of HIV-1 with formalin.

EXAMPLE 1

Virus inactivation of lipid-enveloped viruses with non-ionic detergents Tween® 80 and octyl glucoside Virus preparations of HIV-1, HIV-2, influenza virus and PRV (Pseudorabies virus) were purified via sucrose gradient centrifugation and subsequent dialysis. The purified preparation was admixed with octyl glucoside to a final concentration of 1% or with Tween® 80 to final concentrations of 11%, 15% and 20%, and incubated at 26° C. for 1 hour. Subsequently, the preparation was diluted with PBS, pelletized for 5 min at 400,000 g, and resuspended in PBS prior to titration. HIV-1, HIV-2, influenza virus or PRV treated in this manner were diluted in semi-logarithmic steps in cell culture medium. 8×100 µl of each dilution step were added to a well of a microtiter plate containing indicator cells. The infected cells were incubated at 37° C. for 5 to 6 days, and the cytopathic effect of the virus on the indicator cell was determined microscopically. As the indicator cells, Vero cells were used for PRV and influenza virus, AA2 cells were used for HIV-1, and C8166 cells were used for HIV-2. The $TCID_{50}$ was determined according to Reed and Muench (Am. J. Hyg. 27 (1938), 493–497), and has been summarized in Table 1.

The data of Table 1 indicate that all the viruses tested were inactivated by 5-7 $\log_{10}$ by means of 1% octyl glucoside. Likewise, all the viruses were inactivated by means of 20% of Tween® 80, while for the inactivation of HIV-1, HIV-2 and TBEV already a concentration of 11% of Tween® 80 sufficed for complete inactivation.

TABLE 1

Inactivation of lipid-enveloped viruses by means of the non-ionic detergents Tween ® 80 and octyl glucoside

| | | Virus Titer ($\log_{10}$ $TCID_{50}$/ml) Treatment | | | |
|---|---|---|---|---|---|
| Virus | PBS | 1% Octyl-Glucoside | 11% Tween-80 | 15% Tween-80 | 20% Tween-80 |
| HIV-1 | 6.7 | ≤0.5 | ≤0.5 | ≤0.5 | ≤0.5 |
| HIV-2 | 6.1 | ≤0.5 | ≤0.5 | ≤0.5 | ≤0.5 |
| TBEV | 7.0 | ≤0.5 | ≤0.5 | ≤0.5 | ≤0.5 |
| Influenza | 7.4 | ≤0.5 | 2.9 | ≤0.5 | ≤0.5 |
| PRV | 7.2 | 1.1 | 2.5 | 1.7 | ≤0.5 |

EXAMPLE 2

Kinetics of the virus inactivation of HIV-1 and TBEV after Tween® 80 treatment

A sucrose-gradient-purified virus preparation of TBEV and HIV-1 was mixed with a Tween® 80 solution up to a final concentration of 11% of Tween® 80. The mixture was incubated at 26° C. under continuous stirring, and samples were taken for virus titration after various periods of time. Immediately after having been drawn, the samples were diluted with PBS at a ratio of 1:20, they were pelletized at 400,000 g for 5 min, and the pellet was re-suspended in PBS prior to titration. TBEV was titrated by means of a plaque assay on PS cells, and HIV-1 was titrated on AA2 cells.

The TBE virus was diluted step-wise in log 1-steps, and two aliquots of 500 µl of each dilution step were added to cell monolayers. The cells were overlaid with a 1:1 mixture of 2 x medium and 1.8% carboxymethyl cellulose and incubated for 4 days. Viral plaques were visualized by staining with a 0.1% crystal violet solution, and the titer was determined by counting the plaques.

Titration of HIV-1 on AA2 cells was effected after step-wise dilution in cell culture medium. 8×100 µl of each dilution step were added into the wells of a microtiter plate containing 2×10⁴ AA2 cells. The infected cells were incubated at 37° C. for 5–6 days, and the cytopathic effect of the virus on the indicator cells was determined microscopically. The $TCID_{50}$ was determined according to Reed and Muench (Am. J. Hyg. 27 (1938), 493–497).

The titer (pfu/ml) was determined according to the Poisson distribution. The results are summarized in Table 2.

The data of Table 2 illustrate that by means of 11% Tween® 80 a TBEV preparation is inactivated by >6.4 $\log_{10}$ within 20 minutes at 26° C. Under the same conditions, a HIV preparation is inactivated by >6.2 $\log_{10}$ within 10 minutes

TABLE 2

Kinetics of virus inactivation of HIV-1 and TBEV after treatment with Tween ® 80.

| Duration of treatment (min) | TBEV Titer (PFU/ml) | HIV-1 Titer ($TCID_{50}$/ml) |
|---|---|---|
| 0 | $10^{7.4}$ | $10^{6.7}$ |
| 5 | $10^{3.9}$ | n.b. |
| 10 | $10^{1.5}$ | $<10^{0.5}$ |
| 20 | $<10^{1.0}$ | $<10^{0.5}$ |
| 40 | $<10^{1.0}$ | $<10^{0.5}$ |
| 60 | $<10^{1.0}$ | $<10^{0.5}$ |

EXAMPLE 3

Western blot analysis of inactivated HIV-1 after treatment with 1% octyl glucoside and 11% Tween® 80

A sucrose-gradient-purified preparation of HIV-1 was mixed according to Example 1 with each of 11% Tween® 80, 1-octyl glucoside or PBS, and incubated at 26° C. for 1 hour. Subsequently, the samples were diluted, pelletized for 10 min at 4° C. with 400,000 g (wherein virus proteins, in particular enveloping proteins which become detached from the whole virus by the detergent treatment—the virus particle losing its structural integrity—and remain in the supernatant and thus are no longer apparent in the subsequent Western blot analysis) re-suspended in lysis buffer, separated by means of SDS-PAGE according to Laemmli (Nature 227 (1970), 680–685), and blotted onto a filter membrane.

To detect HIV-1 specific proteins, the filter membrane was incubated over night with a mixture of HIV-1 antibody positive human IgG (Immuno AG), a gp41-specific human monoclonal antibody, and a gp120-specific monoclonal mouse antibody (DuPont). After washing, the membrane was incubated with peroxidase-coupled anti-human and anti-mouse goat-IgG as the second antibody. The detection of HIV-d specific bands was effected via an enzymatic colour reaction with diamino benzidine and $H_2O_2$. The result of the Western blot analysis is illustrated in FIG. 1.

After the treatment with 1k octyl glucoside, HIV-1 enveloping proteins, in particular gp160 and gp120, can no longer be detected, which proves that the structural integrity of the octyl glucoside-treated virus particles and the biological activity of the surface or enveloping proteins have been lost. In contrast thereto, both, in the control (PBS) and in the Tween® 80-treated sample, the enveloping proteins can clearly be detected in the Western blot, which proves that the structural integrity of the whole virus is retained during the Tween treatment. The immune reaction with the gp120-specific antibody also demonstrates that the antigenic determinants of the enveloping proteins are not influenced by the Tween® 80-treatment and do not exhibit any changes as compared to the untreated control.

EXAMPLE 4

Western blot analysis of inactivated KP influenza virus after treatment with 1% octyl glucoside and 15% Tween 80.

A sucrose-gradient-purified preparation of KP influenza virus was treated according to Examples 1 and 3 with 1% octyl glucoside, 15% Tween® 80 or PBS, pelletized, and a Western blot analysis was carried out.

To detect influenza virus-specific proteins, the filter membrane was incubated over night with monoclonal mouse antibodies, directed against HA1 and HA2 of the surface glycoprotein, hemagglutinin (HA). After washing, the membrane was incubated with peroxidase-coupled anti-human and anti-mouse goat IgG as the second antibody. The detection of the influenza virus HA-glycoproteins was effected by means of an enzymatic colour reaction with diamino benzidine and $H_2O_2$.

Figure 2:
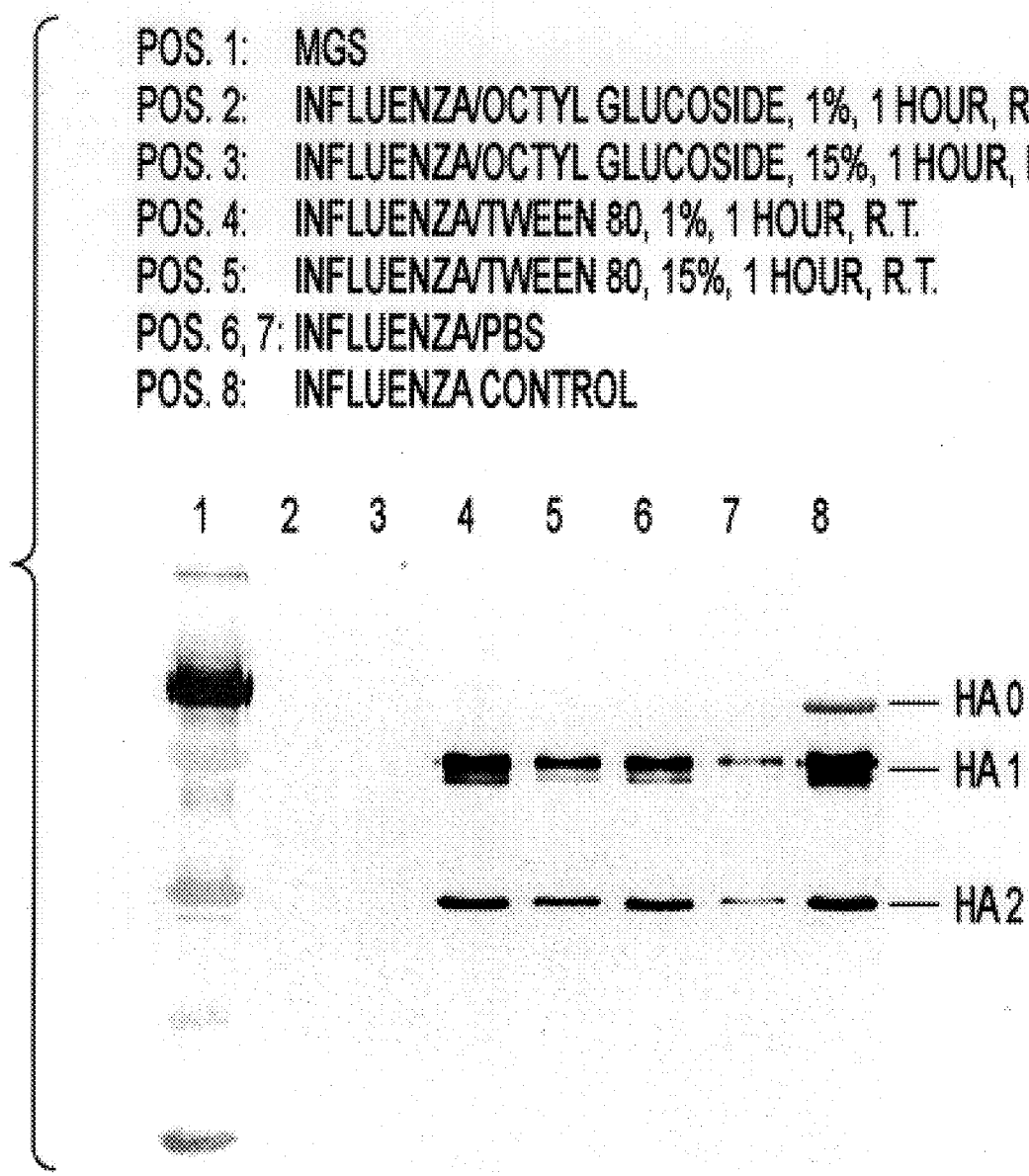
FIG. 2: Western blot analysis of inactivated KP influenza virus following treatment with 1% octyl glucoside and 15% Tween® 80.

The results of the Western blot analysis are illustrated in FIG. 2.

By treatment with 1% octyl glucoside, the HA glycoproteins of influenza virus are completely removed (FIG. 2; columns 2 and 3). In contrast thereto, both in the control (PBS) and in the Tween® 80-treated sample, the structural integrity of the HA glycoproteins can clearly be recognized (FIG. 2, columns 4 to 7).

EXAMPLE 5

Immunization of mice with Tween® 80-inactivated MAIDS complex

A MAIDS complex (BM5-Mix MuLV) preparation was incubated for 1 h with Tween® 80 or with PBS at room temperature. MAIDS complex-sensitive C57 B1/6 were injected i.p. with a Tween® 80-inactivated and a PBS-treated MAIDS complex preparation. 5 and 12 weeks post immunization, the mice were dissected. To judge the MAIDS symptoms, the weight of the cervical lymph nodes and of the spleens was determined, infectious viruses were isolated from the spleen, and the antibody titer against the antigens of the BM5-Mix MuLV-complex was determined. The results are summarized in Tables 3a and 3b.

Tables 3a and 3b show that the treatment of the BM5-Mix MuLV-complex with Tween® 80 led to a complete inactivation. Over the observation period of 12 weeks, no MAIDS symptoms appeared, and no infectious virus could be isolated from the spleen cells. Yet, the inactivated virus preparation did induce relatively high antibody titers against the antigens of the MAIDS complex. The PBS-treated BM5-Mix MuLV preparation gave rise to unambiguous MAIDS symptoms including a large increase of the spleen weight and of the cervical lymph nodes, very high virus titers in the spleen and, on account of the MAIDS-complex-induced immune deficiency, not to any immune response.

TABLE 3a

MAIDS/Results, Tween Inactivation
Resection Results, ELISA-Titer and Isolation of the Ecotropic MuLV from the
Spleens of Infected C57 B1/6-Mice, 5 Weeks post Infection with BM5-Mix MuLV

| Group | Infection | Animal | Resection Enlargement Lymph Nodes | Resection Enlargement Spleen | Weight Spleen | Weight Cervical Lymph Nodes | Elisa - Titer BM5 Mix MuLV-Antigen | log 10 Titer Infected Spleen Cells/ 7.0 Spleen Cells |
|---|---|---|---|---|---|---|---|---|
| A | BM5 Mix MuLV + 11% Tween 80 | 1 | − | − | 70 mg | n.p. | 320 | 0 |
|  |  | 2 | − | − | 60 mg | n.p. | 160 |  |
|  |  | 3 | − | − | 70 mg | n.p. | 80 |  |
|  |  | 4 | − | − | 60 mg | n.p. | 80 |  |
|  |  | 5 | − | − | 70 mg | n.p. | 160 |  |
| B | BM5 Mix MuLV + Buffer | 1 | + | + | 170 mg | 30 mg | < | 3.3 |
|  |  | 2 | + | + | 180 mg | 90 mg | < |  |
|  |  | 3 | + | +/++ | 260 mg | 70 mg | < |  |
|  |  | 4 | + | + | 230 mg | 80 mg | < |  |
|  |  | 5 | + | + | 220 mg | 80 mg | < |  | n.p. = no particularity (weight not determinable); < = <1:10

TABLE 3b

MAIDS/Results, Tween Inactivation
Resection Results, ELISA-Titer and Isolation of the Ecotropic MuLV from the
Spleens of Infected C57 B1/6-Mice, 12 Weeks post Infection with BM5-Mix MuLV

| | | | Resection | | | | Elisa - Titer | log 10 Titer Infected |
|---|---|---|---|---|---|---|---|---|
| | | | Enlargement | | Weight | | BM5 Mix | Spleen Cells/ 7.0 Spleen |
| Group | Infection | Animal | Lymph Nodes | Spleen | Spleen | Cervical Lymph Nodes | MuLV-Antigen | Cells |
| A | BM5 Mix MuLV + 11% Tween 80 | 6 | – | – | 80 mg | n.p. | 80 | 0 |
| | | 7 | – | – | 90 mg | n.p. | 80 | |
| | | 8 | – | – | 70 mg | n.p. | 40 | |
| | | 9 | – | – | 70 mg | n.p. | 40 | |
| | | 10 | – | – | 90 mg | n.p. | 80 | |
| B | BM5 Mix MuLV + Buffer | 6 | +++ | ++ | 630 mg | 610 mg | < | 5.1 |
| | | 7 | +++ | ++/+++ | 710 mg | 660 mg | < | |
| | | 8 | +++/++++ | +++ | 1130 mg | 1190 mg | < | |
| | | 9 | +++ | ++ | 680 mg | 680 mg | < | |
| | | 10 | ++++ | +++ | 990 mg | 1360 mg | < | | n.p. = no particularity (weight not determinable); < = <1:10

EXAMPLE 6

Kinetics of virus inactivation of HIV-1 by means of formalin

To a sucrose-gradient-purified preparation of HIV-1 having a virus titer of $10^7$ TCID$_{50}$/ml, formalin was added at a final concentration of 0.01%, 0.03%, 0.05%, 0.075% and 0.1%. The solution was incubated at 37° C. with continuous stirring, and samples were drawn for virus titration after different intervals. Prior to titration, a corresponding aliquot of $Na_2S_2O$ was added to each of the samples to neutralize formalin. Virus titration was effected as in Example 1.

At a formalin concentration of from 0.03% to 0.1%, an efficient inactivation of HIV-1 occurred after approximately 10 hours. At a concentration of below 0.03% formalin, active, infectious viruses could still be detected after a 30 hour incubation.

TABLE 4

Kinetics of virus inactivation of HIV-1 by means of formalin

| | Time (h) | | | | | | |
|---|---|---|---|---|---|---|---|
| Formalin (%) | 0 | 1 | 3 | 6 | 10 | 20 | 30 |
| 0.01 | 6.0 | 5.9 | 4.9 | 4.1 | 2.9 | 1.0 | 1.0 |
| 0.03 | 5.8 | 3.9 | 2.9 | 1.5 | ≦0.5 | ≦0.5 | ≦0.5 |
| 0.05 | 6.3 | 4.6 | 2.4 | n.d. | ≦0.5 | n.d. | ≦0.5 |
| 0.075 | 6.0 | 4.3 | 1.9 | n.d. | ≦0.5 | n.d. | ≦0.5 |
| 0.10 | 6.4 | 3.7 | 1.6 | n.d. | ≦0.5 | n.d. | ≦0.5 | n.d. = not determined

EXAMPLE 7

Western blot analysis of formalin-inactivated HIV-1 after various periods of incubation From a formalin-inactivated HIV-1 virus preparation according to Example 6, samples were drawn after 0, 1, 2, 3, 6, 10, 20 and 30 hours and a Western blot analysis was carried out with aliquots.

Figure 3A:
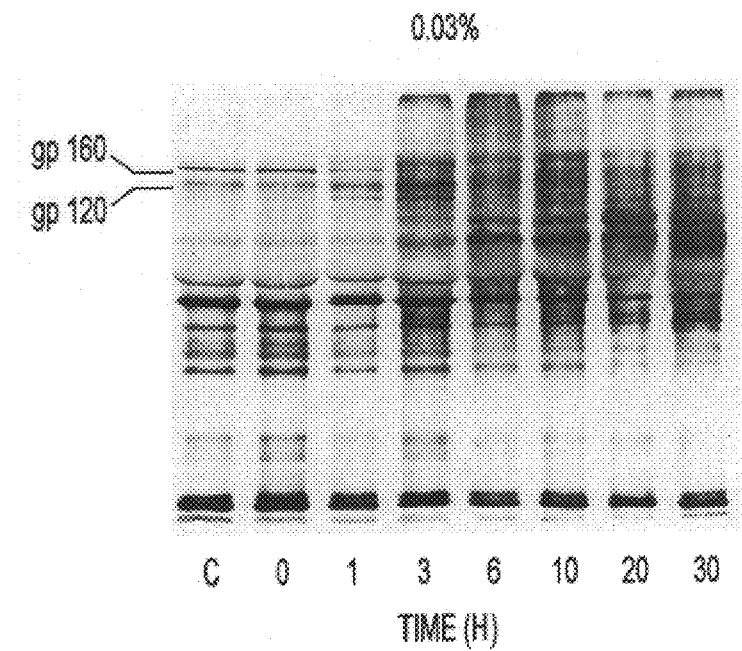
FIG. 3: Western blot analysis of formalin-inactivated HIV-1 after various periods of incubation.
Figure 3B:
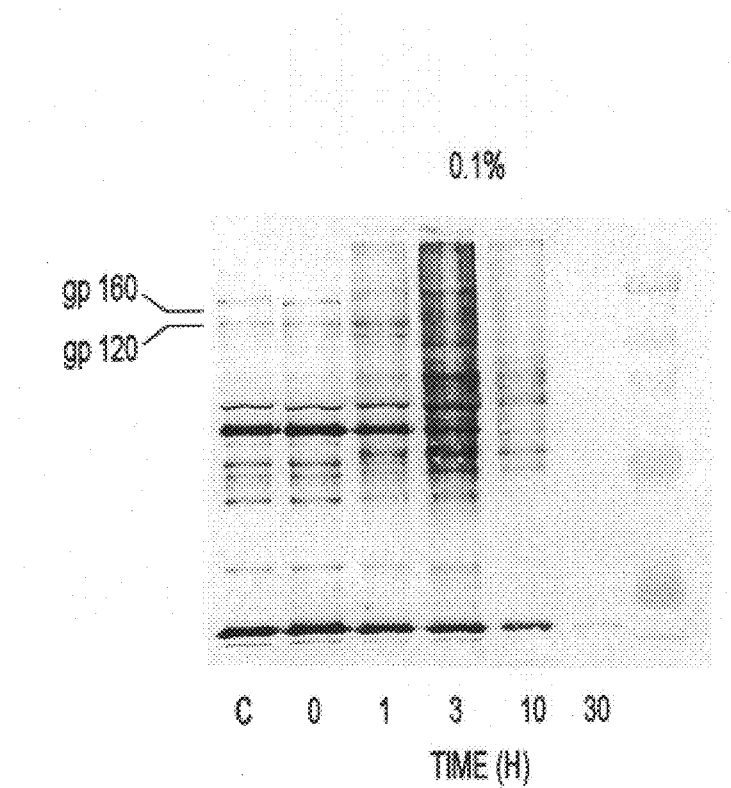

To detect HJV-1-specific proteins, the filter membrane was incubated over night with HIV-1-antibody-positive human IgG (Immuno AG). After washing, the membrane was incubated with peroxidase-coupled anti-human and anti-mouse-goat IgG as the second antibody. The detection of HIV-1-specific bands was effected via an enzymatic colour reaction with diamino benzidine and $H_2O_2$. The result of the Western blot analysis is illustrated in FIG. 3.

It has been shown that after formalin treatment, the viruses can be pelletized and thus are still intact as whole virus, yet already after a 1-hour incubation period with 0.1% formalin, the enveloping proteins are degraded, the native structure of the proteins being destroyed.

Western blot analysis shows that starting from an incubation period of 3 hours, a disintegration of intact viruses occurred. A 10-hour incubation period required according to Example 6 for an efficient inactivation of viruses also leads to a disintegration of the structure of the inactivated viruses.

Thus, it has been shown for the first time that a formalin inactivation strongly affects the intact virus structure.

What is claimed is:

1. A method of inactivating lipid-enveloped viruses comprising
   incubating (i) a whole lipid-enveloped virus having envelope proteins with (ii) a polysorbate selected from the group consisting of Tween® 80, Tween® 40, Tween® 20, and Tween® 60 at a concentration between 1% to 20% for a period of time sufficient to inactivate said lipid-enveloped virus without disintegrating said whole virus, and without destroying the envelope proteins.

2. A method as set forth in claim 1, wherein said lipid-enveloped virus is selected from the group of retroviruses, flaviviruses, orthomyxoviruses, herpes viruses, paramyxoviruses, and arena viruses.

3. A method as set forth in claim 1, wherein said polysorbate is a stabilizing detergent.

4. A method as set forth in claim 1, wherein said whole virus is incubated with said polysorbate for at least 10 minutes.

5. A method as set forth in claim 1, further comprising removing said polysorbate after incubating.

6. A method as set forth in claim 5, wherein said polysorbate is removed by a chromatographic method.

7. A method as set forth in claim 5, wherein said polysorbate is removed by dialysis.

8. A method of preparing an inactivated whole virus, comprising providing an inactivated whole lipid-enveloped virus having envelope proteins, said virus having been inactivated by incubating a whole virus with a polysorbate selected from the group consisting of Tween® 80, Tween® 40, Tween® 20, and Tween® 60 at a concentration between 1% to 20% for a period of time sufficient to inactivate said virus without disintegrating said whole virus, and without destroying the envelope proteins, and admixing said inactivated lipid-enveloped virus with a physiologically acceptable carrier.

9. A method as set forth in claim 8, further comprising admixing said inactivated lipid-envloped virus with an adjuvant.

10. A virus preparation containing inactivated whole lipid-enveloped viruses, wherein the inactivated whole viruses comprise viral envelope proteins that are intact and possess native form and structure.

11. A virus preparation as set forth in claim 10, wherein said viral envelope proteins of said inactivated viruses have an immunogenicity and antigenicity that is not impaired compared to the respective native viruses that have not been inactivated.

12. A virus preparation as set forth in claim 10, further comprising a stabilizing agent.

13. A virus preparation as set forth in claim 12, wherein said stabilizing agent is a polysorbate selected from the group consisting of Tween® 80, Tween® 20, Tween® 60, and Tween® 40.

14. A method of inducing an immune response in a vertebrate comprising administering to the vertebrate a virus preparation containing inactivated whole lipid-enveloped viruses, wherein the inactivated whole lipid-enveloped viruses have been inactivated by incubating a whole lipid-enveloped virus with a polysorbate detergent selected from the group consisting of Tween® 80, Tween® 20, Tween® 60, and Tween® 40 at a concentration between 1% to 20% for a period of time sufficient to inactivate said virus without disintegrating said whole virus.

15. A virus preparation according to claim 13, wherein said polysorbate is contained at a concentration of between 0.05% and 0.5%.

16. A virus preparation according to claim 10, further comprising a physiologically acceptable carrier.

* * * * *